United States Patent
Lozier et al.

(10) Patent No.: US 8,545,499 B2
(45) Date of Patent: Oct. 1, 2013

(54) EXPANDABLE INTRAMEDULLARY ROD

(75) Inventors: Antony J. Lozier, Warsaw, IN (US);
Daniel P. Murphy, Claypool, IN (US);
Justin J. May, Leesburg, IN (US);
Shanon N. Roberts, Warsaw, IN (US);
Andrew L. Gray, Warren, IN (US);
Nicolas J. Pacelli, Cedar Park, TX (US)

(73) Assignee: Zimmer, Inc., Warsaw, IN (US)

( * ) Notice: Subject to any disclaimer, the term of this patent is extended or adjusted under 35 U.S.C. 154(b) by 330 days.

(21) Appl. No.: 12/890,931

(22) Filed: Sep. 27, 2010

(65) Prior Publication Data
US 2011/0077651 A1 Mar. 31, 2011

Related U.S. Application Data

(60) Provisional application No. 61/246,264, filed on Sep. 28, 2009, provisional application No. 61/302,329, filed on Feb. 8, 2010.

(51) Int. Cl.
*A61B 17/58* (2006.01)

(52) U.S. Cl.
USPC .............................. 606/63; 606/62; 606/313

(58) Field of Classification Search
USPC ...................................... 606/62–68, 313, 159
See application file for complete search history.

(56) References Cited

U.S. PATENT DOCUMENTS

| | | | |
|---|---|---|---|
| 3,846,846 A * | 11/1974 | Fischer | 623/23.18 |
| 4,854,312 A | 8/1989 | Raftopoulos et al. | |
| 4,921,484 A * | 5/1990 | Hillstead | 604/104 |
| 5,057,103 A | 10/1991 | Davis | |
| 5,102,413 A * | 4/1992 | Poddar | 606/62 |
| 5,116,335 A | 5/1992 | Hannon et al. | |
| 5,179,915 A | 1/1993 | Cohen et al. | |
| 5,234,433 A | 8/1993 | Bert et al. | |
| 5,441,500 A | 8/1995 | Seidel et al. | |
| 5,445,642 A | 8/1995 | McNulty et al. | |
| 5,578,035 A | 11/1996 | Lin | |
| 5,759,184 A | 6/1998 | Santangelo | |
| 5,810,820 A | 9/1998 | Santori et al. | |
| 5,827,289 A | 10/1998 | Feiley et al. | |
| 5,827,304 A * | 10/1998 | Hart | 606/159 |
| 5,971,986 A | 10/1999 | Santori et al. | |
| 5,972,015 A | 10/1999 | Scribner et al. | |

(Continued)

FOREIGN PATENT DOCUMENTS

| | | |
|---|---|---|
| EP | 2074956 A1 | 7/2009 |
| WO | WO97/18769 A1 | 5/1997 |

(Continued)

OTHER PUBLICATIONS

Written Opinion and International Search Report mailed Dec. 13, 2010 in related International Application No. PCT/US2010/050339.

(Continued)

*Primary Examiner* — Jan Christopher Merene
(74) *Attorney, Agent, or Firm* — Schwegman, Lundberg & Woessner P.A.

(57) ABSTRACT

An expandable rod is provided that is sized for insertion into a patient's bone. A method for using the expandable rod to prepare the patient's bone to receive an orthopedic implant is also provided. The expandable rod is adjustable between a first, contracted state and a second, expanded state, the expansion member expanding radially outwardly from the contracted state to the expanded state.

19 Claims, 11 Drawing Sheets

(56) References Cited

U.S. PATENT DOCUMENTS

| | | | |
|---|---|---|---|
| 6,025,537 A * | 2/2000 | Werding et al. | 623/16.11 |
| 6,066,154 A | 5/2000 | Reiley et al. | |
| 6,126,691 A | 10/2000 | Kasra et al. | |
| 6,200,317 B1 | 3/2001 | Aalsma et al. | |
| 6,224,600 B1 | 5/2001 | Protogirou | |
| 6,235,043 B1 | 5/2001 | Reiley et al. | |
| 6,248,110 B1 | 6/2001 | Reiley et al. | |
| 6,254,571 B1 * | 7/2001 | Hart | 604/107 |
| 6,261,289 B1 | 7/2001 | Levy | |
| 6,355,069 B1 | 3/2002 | DeCarlo, Jr. et al. | |
| 6,454,810 B1 | 9/2002 | Lob | |
| 6,508,841 B2 | 1/2003 | Martin et al. | |
| 6,551,321 B1 | 4/2003 | Burkinshaw et al. | |
| 6,554,833 B2 | 4/2003 | Levy et al. | |
| 6,575,973 B1 | 6/2003 | Shekalim | |
| 6,613,052 B1 | 9/2003 | Kinnett | |
| 6,736,818 B2 | 5/2004 | Perren et al. | |
| 6,767,350 B1 | 7/2004 | Lob | |
| 6,780,185 B2 | 8/2004 | Frei et al. | |
| 6,783,530 B1 | 8/2004 | Levy | |
| 7,052,498 B2 | 5/2006 | Levy et al. | |
| 7,097,648 B1 | 8/2006 | Globerman et al. | |
| 7,241,303 B2 | 7/2007 | Reiss et al. | |
| 7,261,720 B2 | 8/2007 | Stevens et al. | |
| 7,306,607 B2 | 12/2007 | Metzger | |
| 7,507,241 B2 | 3/2009 | Levy et al. | |
| 7,601,152 B2 | 10/2009 | Levy et al. | |
| 7,621,950 B1 * | 11/2009 | Globerman et al. | 623/17.11 |
| 7,699,154 B2 | 4/2010 | Yoshioka | |
| 8,029,522 B2 * | 10/2011 | Ortiz et al. | 606/155 |
| 2002/0032444 A1 | 3/2002 | Mische | |
| 2002/0068939 A1 * | 6/2002 | Levy et al. | 606/63 |
| 2005/0065526 A1 | 3/2005 | Drew et al. | |
| 2005/0085919 A1 | 4/2005 | Durand-Allen et al. | |
| 2005/0143827 A1 | 6/2005 | Globerman et al. | |
| 2005/0209629 A1 | 9/2005 | Kerr et al. | |
| 2006/0084998 A1 | 4/2006 | Levy et al. | |
| 2006/0229617 A1 | 10/2006 | Meller et al. | |
| 2006/0264943 A1 | 11/2006 | Chieng | |
| 2006/0264951 A1 | 11/2006 | Nelson et al. | |
| 2007/0123877 A1 * | 5/2007 | Goldin et al. | 606/62 |
| 2007/0250062 A1 | 10/2007 | Ara Pinilla et al. | |
| 2007/0282443 A1 | 12/2007 | Globerman et al. | |
| 2008/0188897 A1 | 8/2008 | Krebs et al. | |
| 2008/0221575 A1 | 9/2008 | Betts | |
| 2008/0255560 A1 | 10/2008 | Myers et al. | |
| 2008/0262495 A1 | 10/2008 | Coati et al. | |
| 2008/0269746 A1 | 10/2008 | Justin et al. | |
| 2008/0269748 A1 | 10/2008 | Justin et al. | |
| 2008/0269750 A1 | 10/2008 | Justin | |
| 2009/0005782 A1 | 1/2009 | Chirico et al. | |
| 2009/0125028 A1 | 5/2009 | Teisen et al. | |
| 2009/0182336 A1 | 7/2009 | Brenzel et al. | |
| 2010/0023012 A1 | 1/2010 | Voor | |
| 2010/0137925 A1 | 6/2010 | Durand-Allen et al. | |
| 2010/0256640 A1 | 10/2010 | Prygoski et al. | |

FOREIGN PATENT DOCUMENTS

| | | |
|---|---|---|
| WO | WO98/51228 A1 | 11/1998 |
| WO | WO01/28443 A1 | 4/2001 |
| WO | WO03/007830 A1 | 1/2003 |
| WO | WO2007/134248 A1 | 11/2007 |
| WO | WO2009/037471 A2 | 3/2009 |
| WO | WO2009/150691 A1 | 12/2009 |

OTHER PUBLICATIONS

Article "The Effect of Braiding Parameters on the Mechanical Properties of Braided Ropes" Sunay Omeroglu, Fibres & Textile in Eastern Europe, Oct./Dec. 2006, vol. 14, No. 4.

Brochure NexGen Complete Knee Solution, Intramedullary Instrumentation Surgical Technique for the NexGen Cruciate Retaining & Legacy Posterior Stabilized Knee, Zimmer, Inc. 1995, 1997, 1998.

Brochure "Zimmer MIS Multi-Reference 4-in-1 Femoral Instrumentation Surgical Technique for NexGen Cruciate Retaining & NexGen Legacy Posterior Stabilized Knees", 97-5967-002-00 Rev. 6 5ML, Zimmer 2003, 2005, 2008.

* cited by examiner

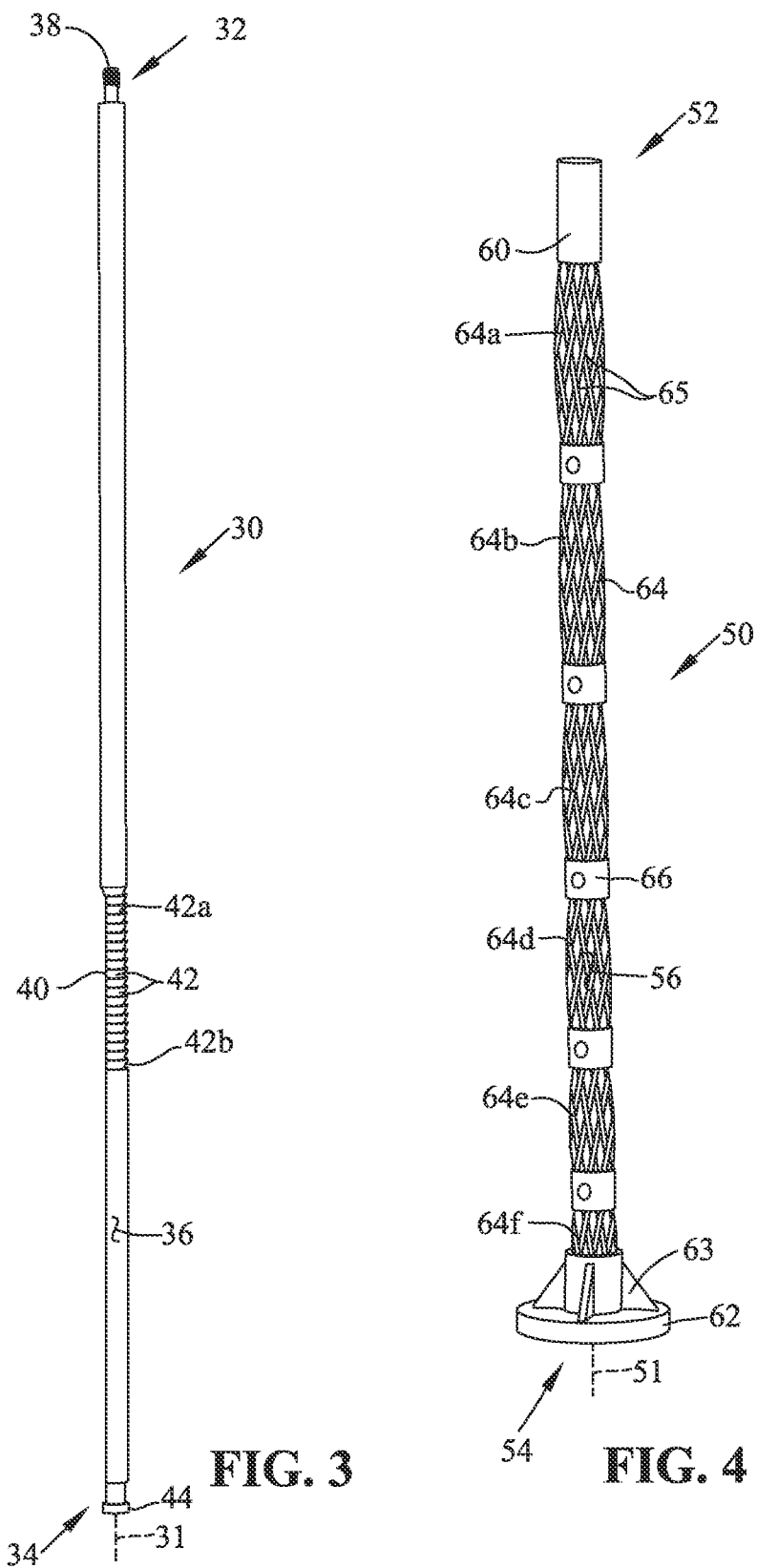

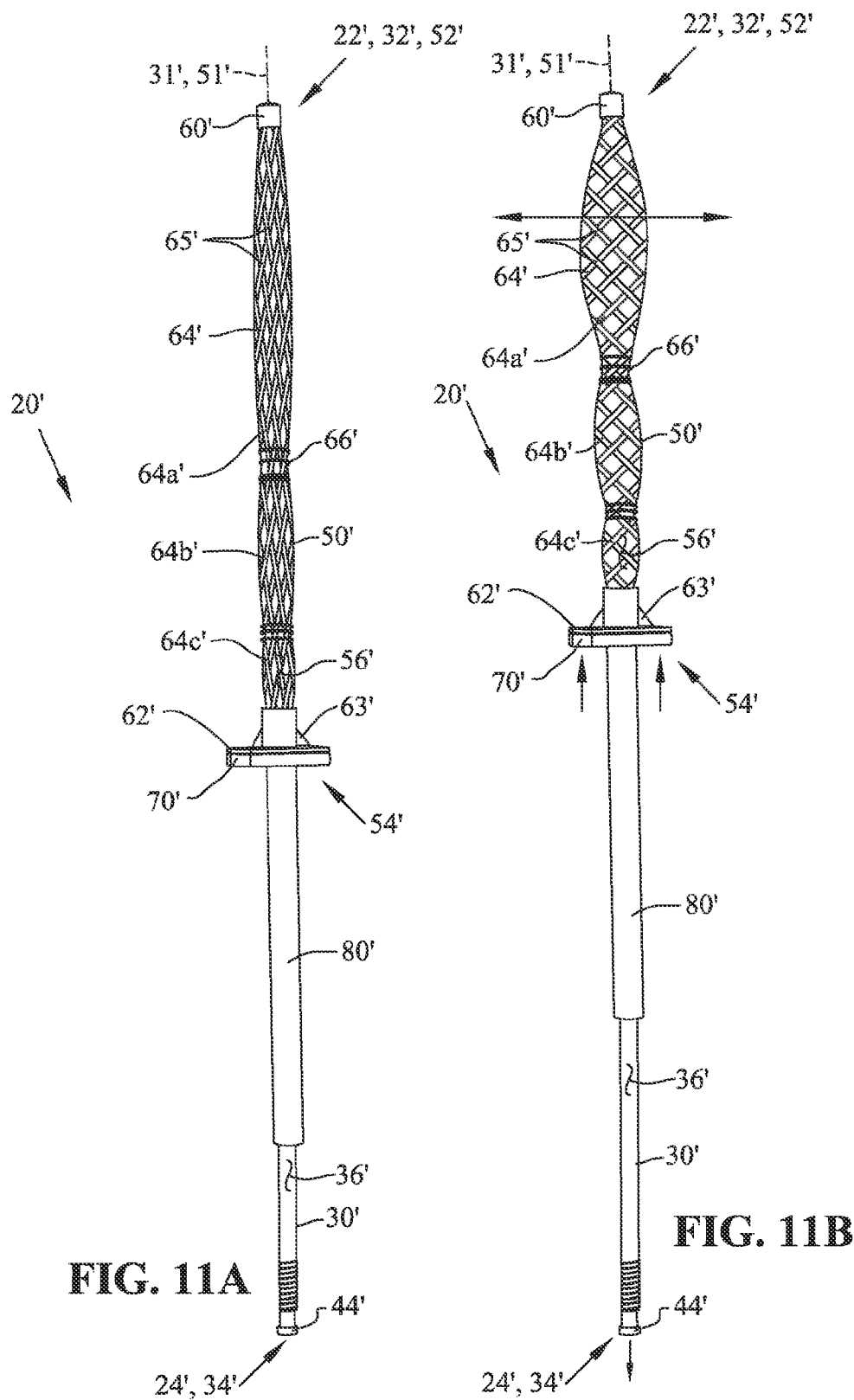

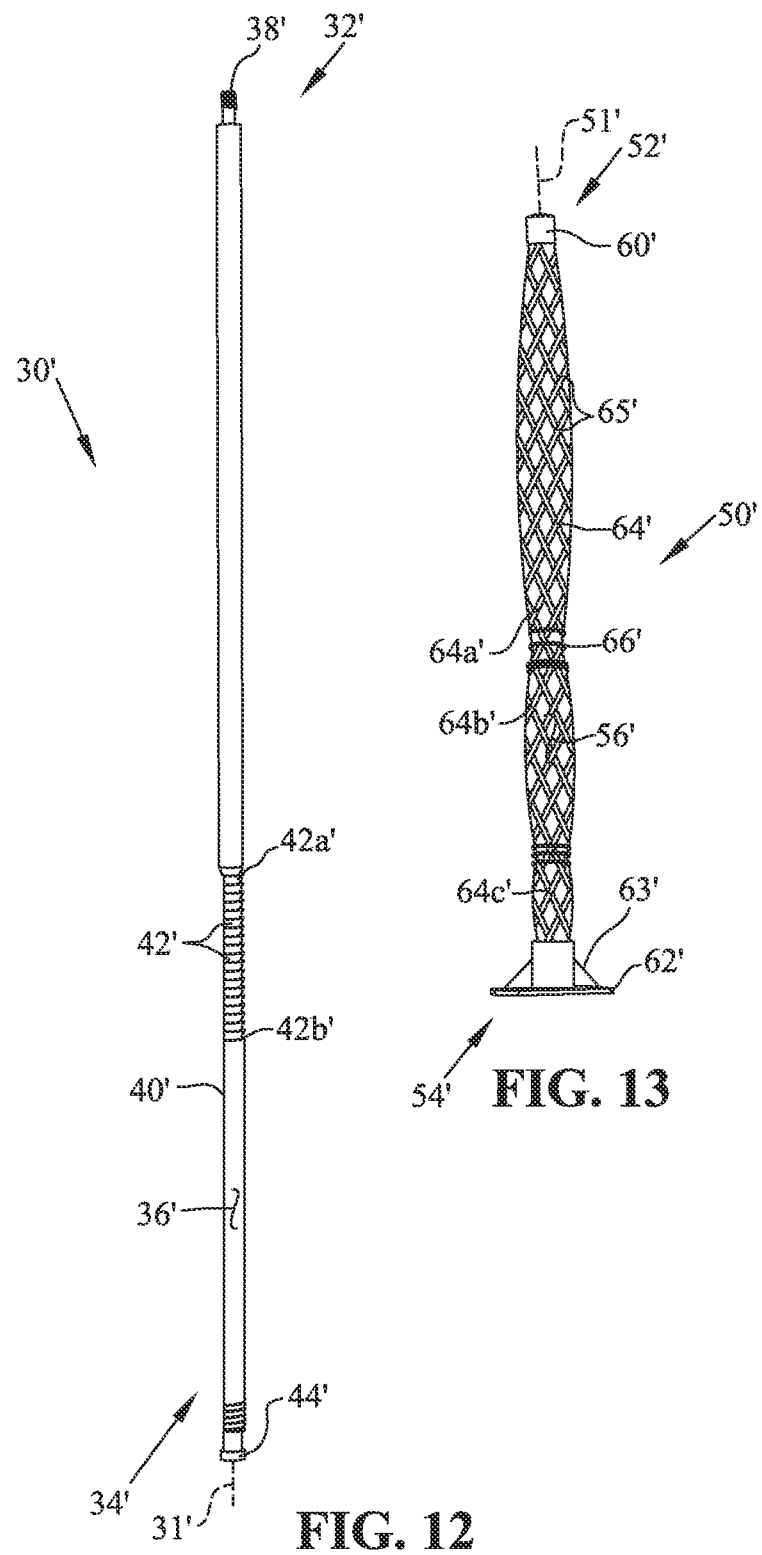

EXPANDABLE INTRAMEDULLARY ROD

CROSS REFERENCE TO RELATED APPLICATIONS

This application claims priority from U.S. Provisional Patent Application Ser. No. 61/246,264, filed Sep. 28, 2009, and U.S. Provisional Patent Application Ser. No. 61/302,329, filed Feb. 8, 2010, both entitled "EXPANDABLE INTRAMEDULLARY ROD," the disclosures of which are hereby expressly incorporated by reference herein in their entirety.

BACKGROUND

1. Field of the Invention

The present invention relates to the field of orthopedic guides. In particular, the present invention relates to an orthopedic guide assembly including an expandable intramedullary rod and to a method for using the same.

2. Description of the Related Art

Preparing a bone to receive an implant requires accurate resection and shaping of the bone. For example, in a knee arthroplasty procedure, preparing a distal femur to receive a femoral implant requires accurate resection and shaping of the distal femur. Accurate preparation of the distal femur ensures that the femoral implant will rest properly against the distal femur and articulate properly with the adjacent tibial implant to replicate movement and stability of the natural knee joint. Therefore, orthopedic guides used to prepare the bone, including cut guides and drill guides, must be properly aligned and secured to the bone. During a knee arthroplasty procedure, for example, an intramedullary rod may be used to align and secure an orthopedic guide to the distal femur.

SUMMARY

The present invention provides an expandable rod that is sized for insertion into a patient's bone and a method for using the same to prepare the patient's bone to receive an orthopedic implant. The expandable rod is adjustable between a first, contracted state and a second, expanded state, the expansion member expanding radially outwardly from the contracted state to the expanded state.

According to an embodiment of the present invention, an expandable rod is provided that is sized for insertion into a patient's bone. The expandable rod includes a shaft having a first end and a second end, an expansion member coupled to the shaft and adjustable between a first, contracted state and a second, expanded state, the expansion member expanding radially outwardly from the contracted state to the expanded state, the expansion member including a first expansion segment and a second expansion segment, the first expansion segment having a higher slenderness ratio than the second expansion segment, and an actuator moveably coupled to the shaft to adjust the expansion member between the contracted state and the expanded state.

According to another embodiment of the present invention, an expandable rod is provided that is sized for insertion into a patient's bone. The expandable rod includes an expansion member having a first end and a second end, a shaft coupled to the expansion member, and an actuator moveably coupled to the shaft, the actuator configured to move the second end of the expansion member axially toward the first end of the expansion member to compress the expansion member axially and to expand the expansion member radially outwardly, the first end of the expansion member expanding before the second end of the expansion member.

According to yet another embodiment of the present invention, a method is provided for preparing a patient's bone to receive an orthopedic implant. The method includes the steps of providing an expandable rod that includes a shaft and an expansion member having a first end and a second end, the expansion member of the expandable rod adjustable between a first, contracted state and a second, expanded state, inserting the expandable rod into the patient's bone with the expansion member in the contracted state, after the inserting step, expanding the expansion member radially outwardly to the expanded state, the first end of the expansion member expanding before the second end of the expansion member, at least a portion of the shaft remaining outside of the patient's bone, coupling a guide component to the portion of the shaft remaining outside of the patient's bone, and resecting the patient's bone using the guide component.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 3 is a plan view of the shaft of FIG. 2A;

FIG. 4 is a plan view of the expansion sleeve of FIG. 2A including a sliding washer;

FIG. 11A is a plan view of another exemplary orthopedic guide assembly of the present invention including an expansion sleeve, a shaft, and an actuator, the orthopedic guide assembly shown with the expansion sleeve in a first, insertion position;

FIG. 11B is another plan view of the orthopedic guide assembly of FIG. 11A, shown with the expansion sleeve in a second, expanded and locked position;

FIG. 12 is a plan view of the shaft of FIG. 11A;

FIG. 13 is a plan view of the expansion sleeve of FIG. 11A including a sliding washer;

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
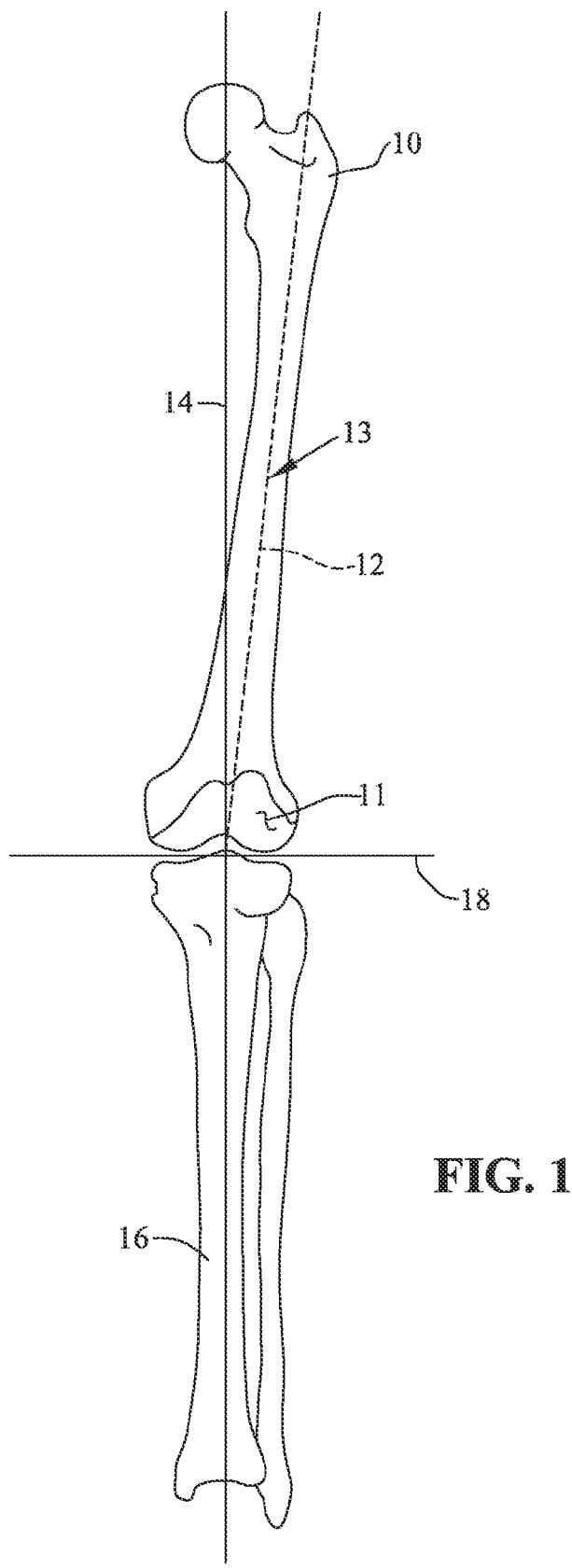
FIG. 1 is an anterior elevational view of a knee joint formed between a femur and a tibia.
Figures 2A, 2B:
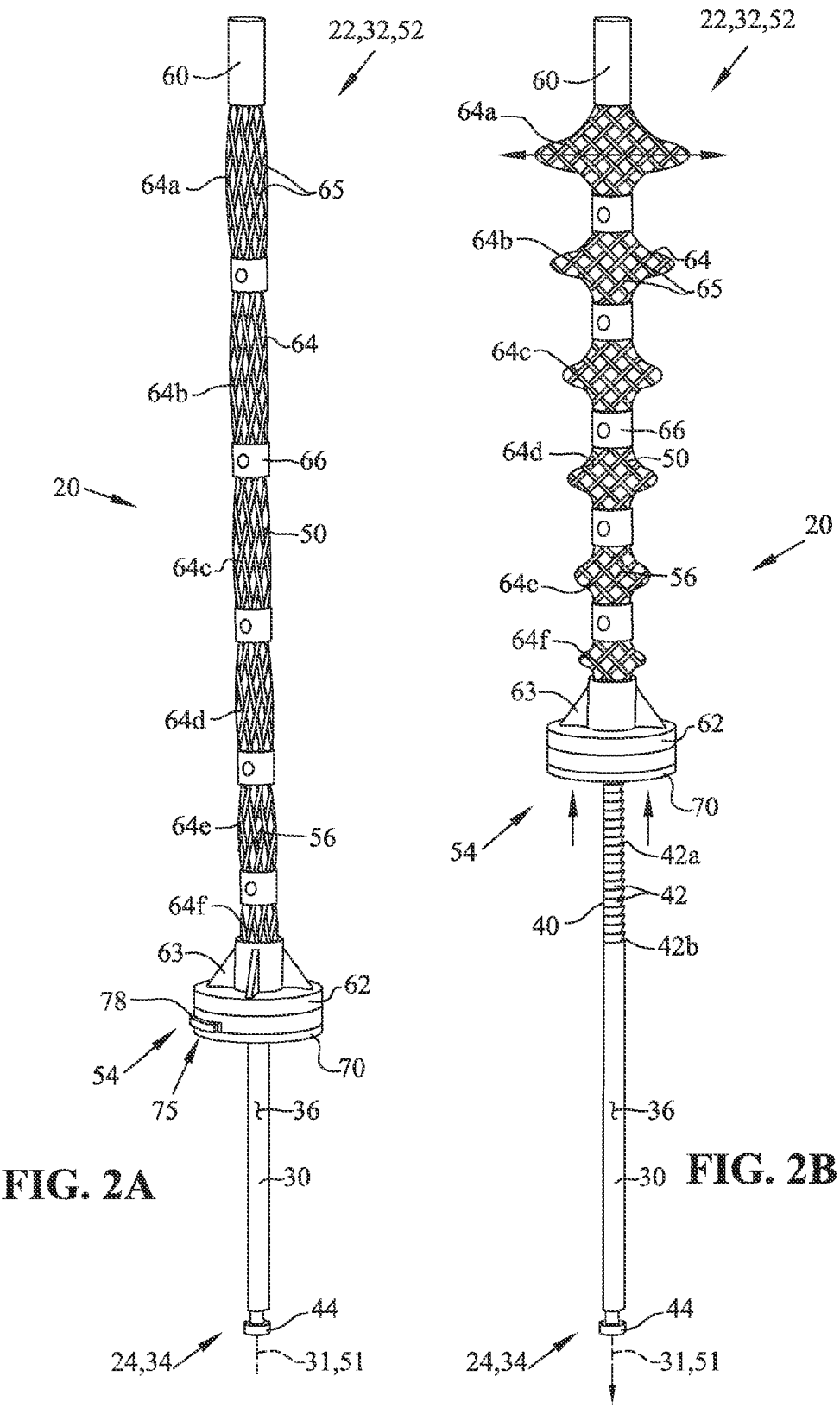
FIG. 2A is a plan view of an exemplary orthopedic guide assembly of the present invention including an expansion sleeve, a shaft, and an actuator, the orthopedic guide assembly shown with the expansion sleeve in a first, insertion position.
FIG. 2B is another plan view of the orthopedic guide assembly of FIG. 2A, shown with the expansion sleeve in a second, expanded and locked position.

Referring to FIGS. 1, 2A, and 2B, the present invention provides an orthopedic guide assembly 20 used to prepare a bone to receive an implant. For example, orthopedic guide assembly 20 of the present invention may be used to prepare femur 10 of FIG. 1 to receive a femoral implant (not shown). While orthopedic guide assembly 20 is described and depicted herein as being implanted into femur 10, orthopedic guide assembly 20 may be implanted into other long bones of the body, such as a patient's tibia, humerus, ulna, or radius, for example.

A natural knee joint is shown in FIG. 1 between femur 10 and tibia 16. Femur 10 includes exterior surface 11, anatomic axis 12, and mechanical axis 14. Femur 10 also includes intramedullary canal 13 that extends through the center of femur 10 along anatomic axis 12. To replicate natural movement and stability of the knee joint, femur 10 should be resected along transverse axis 18, which extends perpendicular to mechanical axis 14 and parallel to the resected surface of tibia 16.

Figure 9:
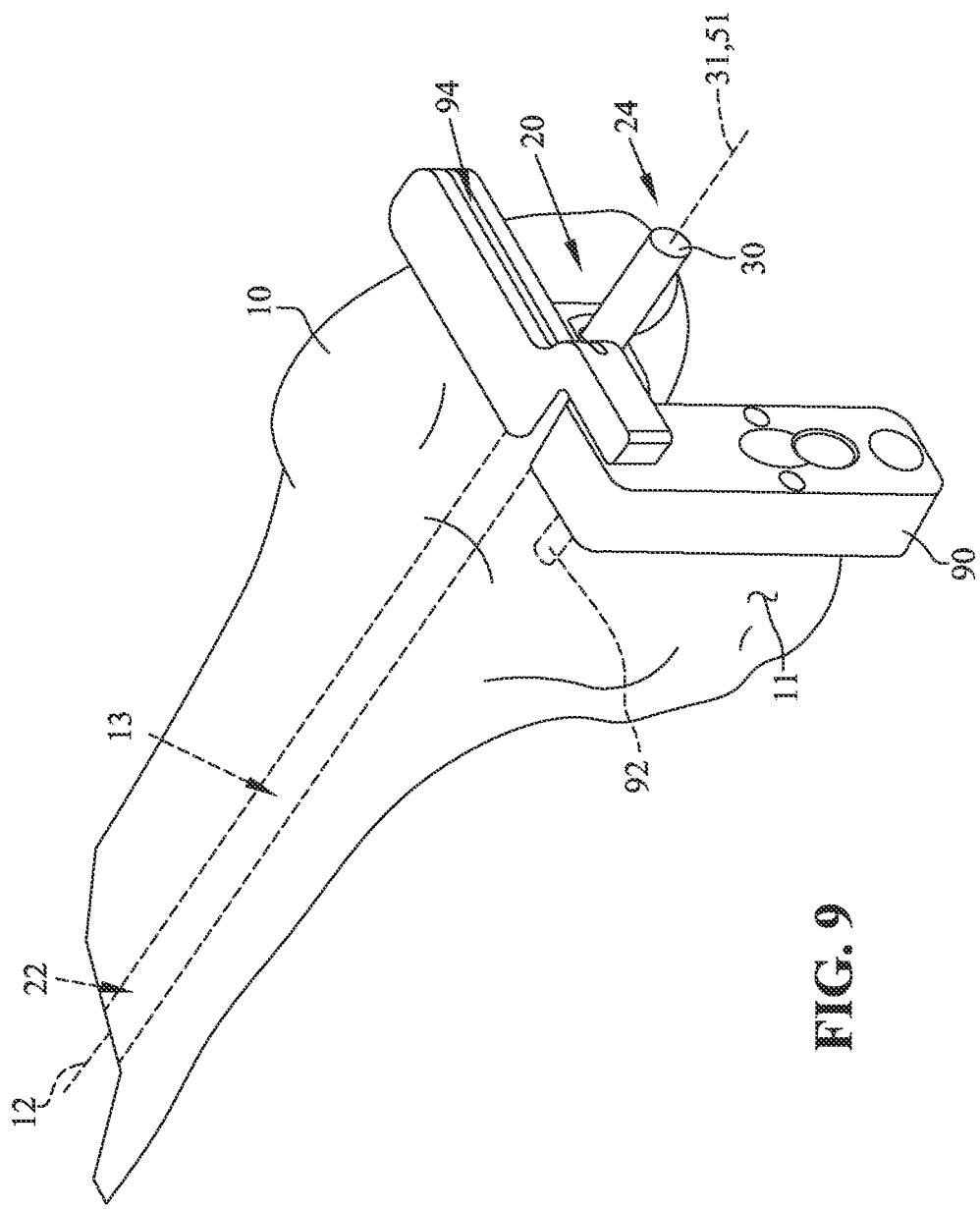
FIG. 9 is a perspective view similar to FIG. 8, further including a guide component of the orthopedic guide assembly referencing an exterior surface of the femur.
Figure 10:
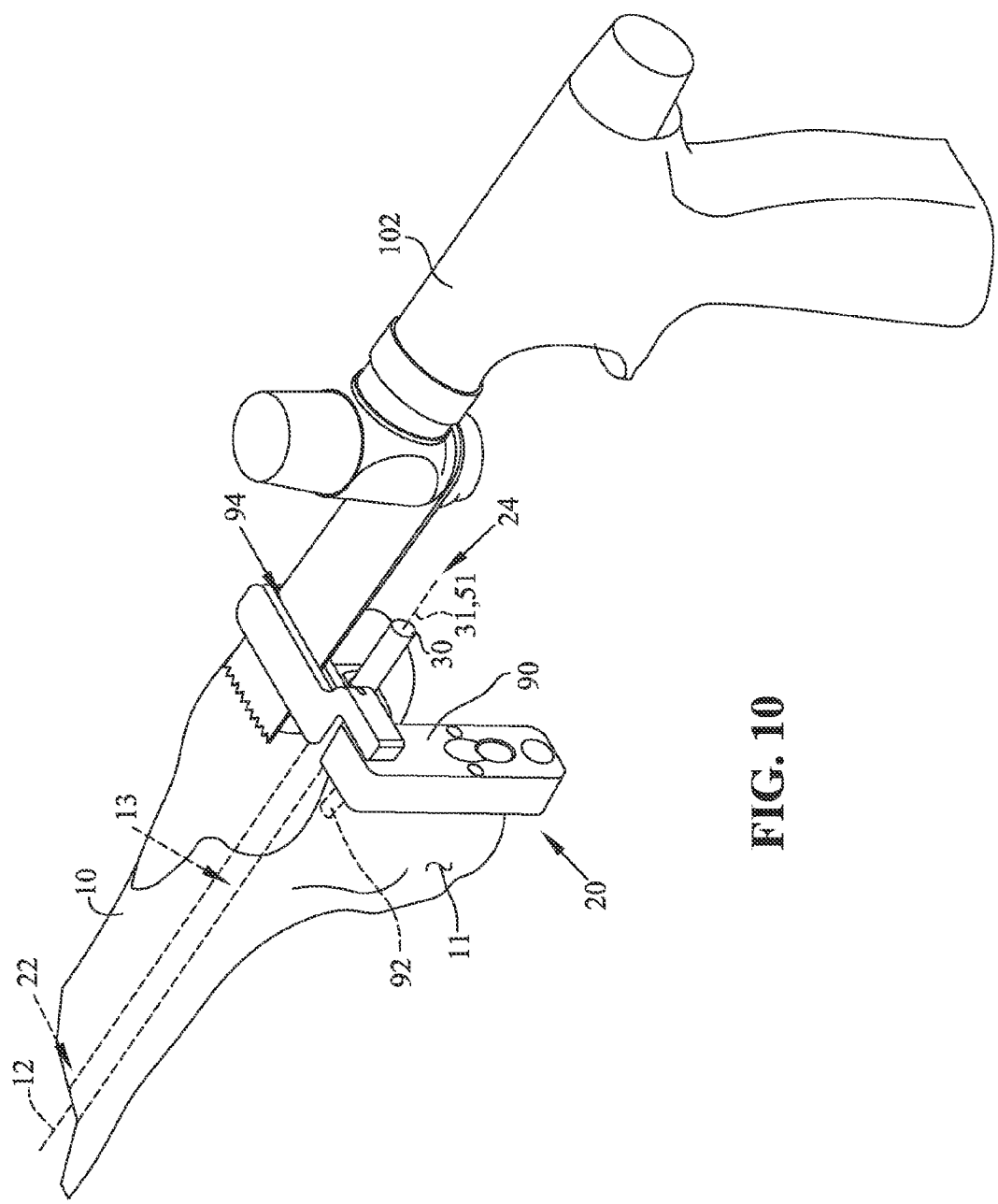
FIG. 10 is a perspective view similar to FIG. 9, further including an oscillating saw resecting the exterior surface of the femur.
Figure 14:
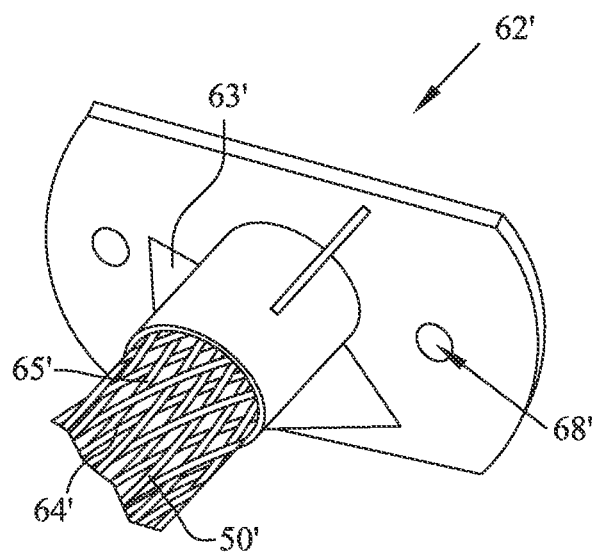
FIG. 14 is a perspective view of the expansion sleeve and the sliding washer of FIG. 13.

As shown in FIGS. 2A and 2B, orthopedic guide assembly 20 has first end 22 and second end 24. Orthopedic guide assembly 20 includes shaft 30 (FIG. 3), expansion sleeve 50 (FIGS. 4 and 5), actuator 70 (FIG. 6), and guide component 90 (FIGS. 9 and 10). Each component of orthopedic guide assembly 20 is described further below.

Elongate shaft 30 of orthopedic guide assembly 20 is illustrated in FIG. 3. Shaft 30 includes longitudinal axis 31, first end 32, second end 34, and outer periphery 36. Shaft 30 may be constructed of a biocompatible metal, a rigid biocompatible polymer, or another suitable biocompatible material. It is also within the scope of the present invention that shaft 30 may be a flexible device configured to curve or bend to accommodate contoured bones. The flexible shaft 30 may be of the type disclosed in U.S. patent application Ser. No. 11/244,640, filed Oct. 6, 2005, entitled "FLEXIBLE SHAFT," the disclosure of which is expressly incorporated by reference herein.

First end 32 of shaft 30 includes external thread 38. Second end 34 of shaft 30 includes flat 40 that extends about a portion of outer periphery 36 in an axial direction along shaft 30. Second end 34 of shaft 30 also includes a plurality of teeth 42. According to an exemplary embodiment of the present invention, teeth 42 extend across approximately 1" of shaft 30 and adjacent teeth 42 are spaced apart by approximately 0.0625", although the spacing of teeth 42 may vary. Also, each tooth 42 includes blocking face 42a that faces first end 32 of shaft 30 and angled face 42b that faces second end 34 of shaft 30. Optionally, second end 34 of shaft 30 may further include a linear reference scale (not shown) that corresponds with teeth 42. Also, second end 34 of shaft 30 may include an optional coupling feature 44 configured to receive an actuating tool (not shown). Coupling feature 44 may include a protrusion, as shown in FIG. 3, or a groove, for example.

Expansion sleeve 50 of orthopedic guide assembly 20 is illustrated in FIG. 4. Expansion sleeve 50 includes longitudinal axis 51, first end 52, second end 54, and outer periphery 56. Expansion sleeve 50 also defines an internal channel (not shown) that extends along longitudinal axis 51. The internal channel of expansion sleeve 50 is sized to receive shaft 30 therein such that first end 52 of expansion sleeve 50 is positioned adjacent to first end 32 of shaft 30 and second end 54 of expansion sleeve 50 is positioned adjacent to second end 34 of shaft 30, as shown in FIG. 2A.

First end 52 of expansion sleeve 50 includes an internally threaded plug 60 that is configured to engage external thread 38 of first end 32 of shaft 30. Once assembled, first end 52 of expansion sleeve 50 is axially fixedly coupled to first end 32 of shaft 30. Plug 60 may be a rigid or flexible component that acts as a skirt to control the shape of expansion sleeve 50 when expanded outwardly, as described further below.

Figure 5:
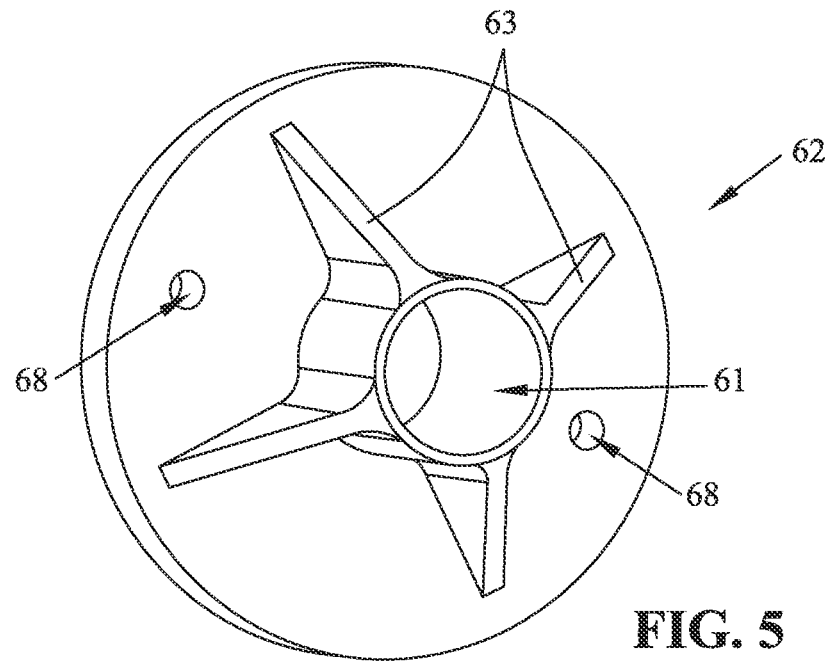
FIG. 5 is a perspective view of the sliding washer of FIG. 4.

Second end 54 of expansion sleeve 50 includes sliding washer 62, as shown in FIGS. 4 and 5. Sliding washer 62 defines internal channel 61 that is sized to receive shaft 30 therein, as shown in FIG. 2A. Once assembled, sliding washer 62 is configured to translate freely axially along second end 34 of shaft 30, including flat 40 of shaft 30 and teeth 42 of shaft 30. Therefore, internal channel 61 of sliding washer 62 may be sized to avoid engaging teeth 42 of shaft 30. Sliding washer 62 also includes sharpened fins 63 that extend from the side of sliding washer 62 that faces first end 52 of expansion sleeve 50. Sliding washer 62 further includes attachment apertures 68 for aligning and receiving actuator 70, as described further below.

Between first end 52 and second end 54, expansion sleeve 50 includes braid 64 that is biased naturally in a radially contracted state, as shown in FIG. 4. Braid 64 includes a plurality of intertwined strands 65 extending in directions angled to longitudinal axis 51 of expansion sleeve 50. For example, strands 65 of braid 64 may have braid angles of approximately 10 degrees to 85 degrees relative to longitudinal axis 51 of expansion sleeve 50. A low braid angle has a low axial contribution and may result in a stiffer product lengthwise, while a high braid angle may improve radial hoop strength. Braid 64 may also include axial strands (not shown) extending parallel to longitudinal axis 51 of expansion sleeve 50. Expansion sleeve 50 may include any suitable number of strands 65, such as about 10, 15, 20, 25, 30, 35, 40, or more strands 65. Strands 65 of braid 64 may be woven together in a desired pattern and orientation. For example, braid 64 may have a 1/1 pattern, a 2/2 pattern, an axial pattern, or combinations thereof. Strands 65 of braid 64 may be in the form of wires, yarns, or fibers, for example. Strands 65 of braid 64 may be constructed of a biocompatible metal, such as Nitinol, titanium, tantalum, or stainless steel, a biocompatible polymer, or another suitable biocompatible material, and strands 65 of braid 64 may be round or flat, for example. An exemplary flat strand 65 is rectangular in cross-section, having a cross-sectional length of approximately 0.030" and a cross-sectional width of approximately 0.010", although the cross-sectional area of each strand 65 may vary.

Optionally, expansion sleeve 50 also includes one or more annular bands 66 that wrap around braid 64 and divide braid 64 into a plurality of discrete braid segments 64a-f. In the illustrated embodiment of FIG. 4, expansion sleeve 50 includes five annular bands 66 that divide braid 64 into six braid segments 64a-f. Bands 66 may be constructed of a biocompatible metal, such as stainless steel, a biocompatible polymer, or another suitable biocompatible material. Bands 66 may be rigid or flexible. Also, bands 66 may be solid or partially open.

Bands 66 may be axially spaced across expansion sleeve 50 at even intervals or varied intervals. For example, as shown in FIG. 4, bands 66 are spaced further apart at first end 52 of expansion sleeve 50 than at second end 54 of expansion sleeve 50 such that braid segments 64a-c at first end 52 of expansion sleeve 50 are progressively longer than braid segments 64d-f at second end 54 of expansion sleeve 50. According to an exemplary embodiment of the present invention, braid segment 64a located nearest to first end 52 of expansion sleeve 50 may have a length of approximately 1.375", while braid segment 64f located nearest to second end 54 of expansion sleeve 50 may have a length of approximately 0.600".

Also, bands 66 may be axially fixedly coupled to braid 64, such as with a mechanical connection, an epoxy, or an adhesive, or bands 66 may be free to translate axially across braid 64. Permitting bands 66 to translate across braid 64 may allow a surgeon to intraoperatively customize the length of braid segments 64a-f and/or to block specific areas of braid 64 from expanding with bands 66 to accommodate a patient's specific needs.

Figure 6:
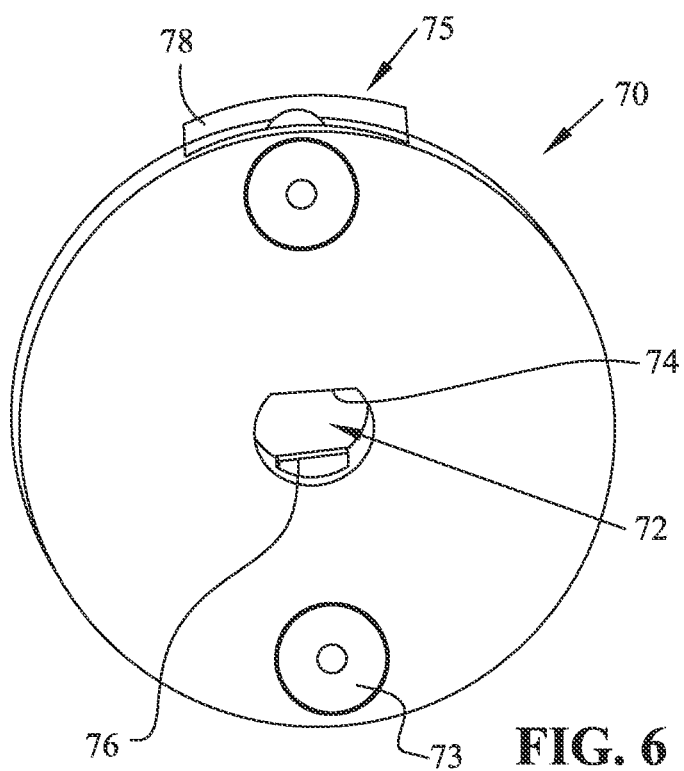
FIG. 6 is a perspective view of the actuator of FIG. 2A.

Actuator 70 of orthopedic guide assembly 20 is illustrated in FIG. 6. Actuator 70 defines internal channel 72 that is sized to receive shaft 30 therein, as shown in FIG. 2A. Internal channel 72 of actuator 70 is partially defined by flat wall 74. Once assembled, actuator 70 is configured to translate axially along second end 34 of shaft 30, with flat wall 74 of actuator 70 cooperating with flat 40 of shaft 30 to prevent actuator from rotating freely about shaft 30.

As shown in FIGS. 2A and 2B, actuator 70 is configured to attach to second end 54 of expansion sleeve 50. More particularly, actuator 70 is configured to couple to sliding washer 62 on second end 54 of expansion sleeve 50. For example, as shown in FIGS. 5 and 6, actuator 70 includes pins 73 that may be screwed into attachment apertures 68 of sliding washer 62. In this embodiment, sliding washer 62 and actuator 70 are configured to translate axially together along second end 34 of shaft 30. Because actuator 70 is prevented from rotating freely about shaft 30, sliding washer 62 attached to actuator 70 is also prevented from rotating freely about shaft 30. As a result, expansion sleeve 50 is also prevented from rotating freely about shaft 30.

Actuator 70 further includes locking assembly 75 that maintains the axial position of actuator 70 along shaft 30. In the illustrated embodiment of FIG. 6, locking assembly 75 includes cam surface 76 that is spring-biased toward shaft 30 to engage teeth 42 of shaft 30. Locking assembly 75 also includes release button 78.

According to an exemplary embodiment of the present invention, and as shown in FIGS. 2A and 2B, locking assembly 75 of actuator 70 and teeth 42 of shaft 30 cooperate to allow actuator 70 to translate forward toward first end 52 of expansion sleeve 50 but to prevent actuator 70 from translating backward away from first end 52 of expansion sleeve 50. Also, because sliding washer 62 on second end 54 of expansion sleeve 50 is attached to actuator 70, second end 54 of expansion sleeve 50 is able to translate forward toward first end 52 of expansion sleeve 50 but is prevented from translating backward away from first end 52 of expansion sleeve 50. To permit forward movement of actuator 70 toward first end 52 of expansion sleeve 50, cam surface 76 (FIG. 6) is configured to slide across angled faces 42b of teeth 42. After passing over that angled face 42b, locking assembly 75 (FIG. 6) springs back into place to engage the next tooth 42, thereby maintaining actuator 70 in a discrete axial position along shaft 30. To block backward movement of actuator 70 away from first end 52 of expansion sleeve 50, cam surface 76 (FIG. 6) is configured to abut blocking faces 42a of teeth 42.

Locking assembly 75 may be released by pressing release button 78 to raise cam surface 76 away from teeth 42 of shaft 30. In this released state, actuator 70 is free to translate backward along shaft 30 and away from first end 52 of expansion sleeve 50. In fact, actuator 70 may be forced backward along shaft 30 under the natural force of the contracting expansion sleeve 50.

In operation, orthopedic guide assembly 20 may be adjusted from a first, insertion or contracted position, as shown in FIG. 2A, to a second, expanded position, as shown in FIG. 2B. In the insertion position of FIG. 2A, expansion sleeve 50 rests naturally against shaft 30. More particularly, braid 64 of expansion sleeve 50 rests naturally against shaft 30. In the expanded position of FIG. 2B, the surgeon moves actuator 70 and sliding washer 62 on second end 54 of expansion sleeve 50 toward first end 52 of expansion sleeve 50 to axially compress expansion sleeve 50, forcing braid 64 of expansion sleeve 50 to expand radially outwardly from shaft 30. Adjacent strands 65 of braid 64 will also move apart in a direction perpendicular to longitudinal axis 51.

According to an exemplary embodiment of the present invention, if braid segments 64a-f are provided in various lengths, braid segments 64a-f will expand to different diameters. For example, as shown in FIG. 2B, the longer braid segments 64a-c located near first end 52 of expansion sleeve 50 will expand to a greater diameter than the shorter braid segments 64d-f located near second end 54 of expansion sleeve 50.

Figure 7:
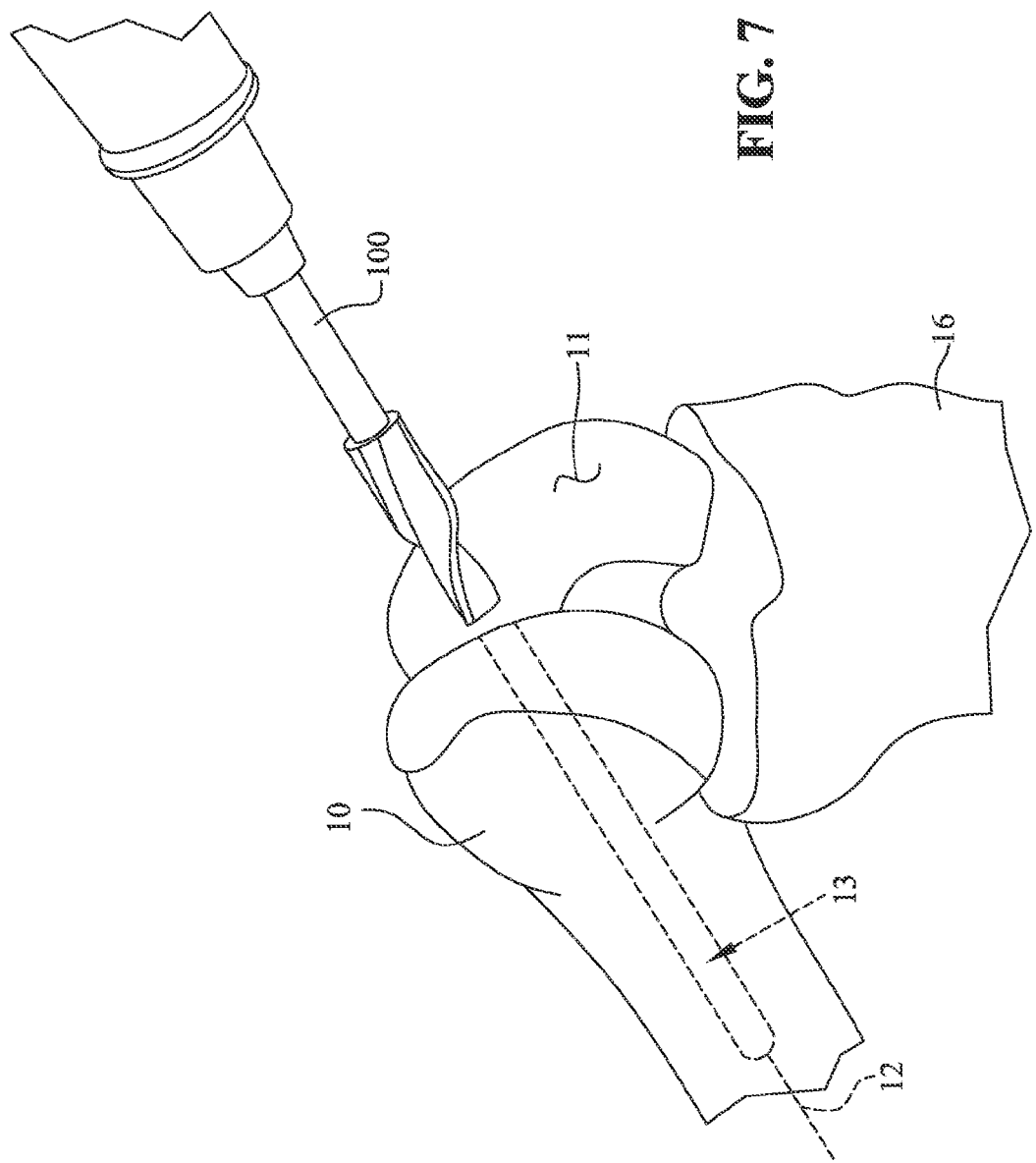
FIG. 7 is a perspective view of the knee joint of FIG. 1, further including a drill preparing an intramedullary canal of the knee joint.

Referring next to FIGS. 7-10, an exemplary surgical method of using orthopedic guide assembly 20 is illustrated. First, as shown in FIG. 7, the surgeon prepares intramedullary canal 13 of femur 10 by drilling into the distal portion of femur 10 with drill 100. The surgeon may drill a hole having a diameter of approximately 0.2", 0.3", 0.4", or more into the distal portion of femur 10. According to an exemplary embodiment of the present invention, the prepared intramedullary canal 13 extends substantially parallel to anatomic axis 12 of femur 10. After drilling, the surgeon may suction the prepared intramedullary canal 13 to remove fluid and/or debris.

Figure 8:
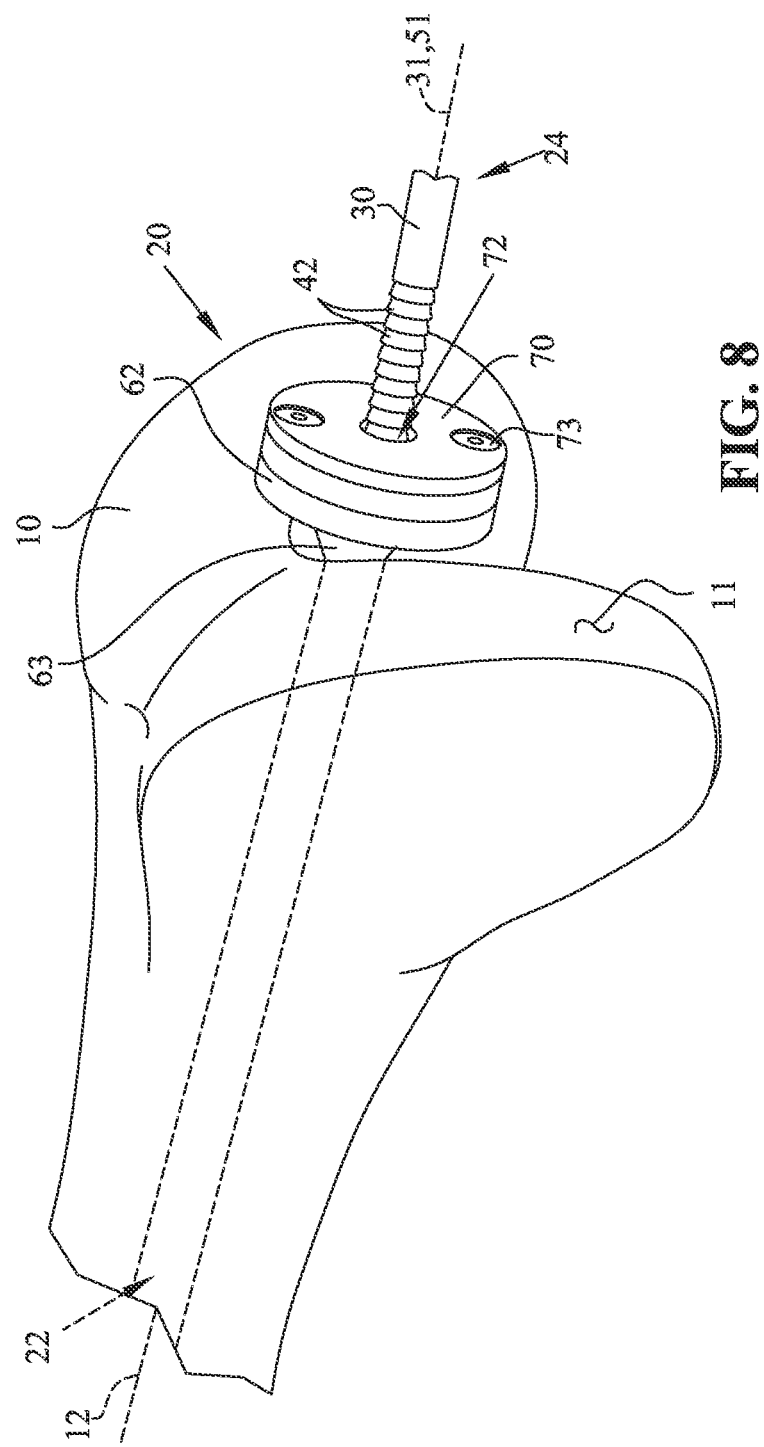
FIG. 8 is a perspective view of the orthopedic guide assembly of FIG. 2A inserted into the prepared intramedullary canal of FIG. 7.

Next, with orthopedic guide assembly 20 in the first, insertion position of FIG. 2A, the surgeon inserts orthopedic guide assembly 20 into the prepared intramedullary canal 13 of femur 10. More particularly, the surgeon inserts first end 22 of orthopedic guide assembly 20 into the prepared intramedullary canal 13 of femur 10, with second end 24 of orthopedic guide assembly 20 facing the surgeon and tibia 16 (FIG. 1), as shown in FIG. 8. It is also within the scope of the present invention that the surgeon may first insert expansion sleeve 50 into femur 10, followed by shaft 30. Shaft 30 of orthopedic guide assembly 20 should be sufficiently long to reproduce anatomic axis 12 of femur 10 when implanted in femur 10. For example, shaft 30 may be provided in lengths of approximately 6", 7", 8", 9", 10", or more.

It is within the scope of the present invention that first end 22 of orthopedic guide assembly 20 may be externally threaded or fluted so that the surgeon may simultaneously drill into intramedullary canal 13 of femur 10 and insert orthopedic guide assembly 20 therein. For example, referring to FIG. 2A, plug 60 on first end 52 of expansion sleeve 50 may be a drill bit configured to drill into intramedullary canal 13 of femur 10. This would eliminate the initial step of pre-drilling intramedullary canal 13.

It is also within the scope of the present invention that shaft 30 may be cannulated to facilitate removal of fluid and/or debris from the prepared intramedullary canal 13 of femur 10 after implantation. Also, plug 60 on first end 52 of expansion sleeve 50 may be configured to vent excess pressure from intramedullary canal 13 of femur 10.

After the surgeon inserts orthopedic guide assembly 20 into the prepared intramedullary canal 13 of femur 10, the surgeon adjusts orthopedic guide assembly 20 to the second, expanded position of FIG. 2B. The surgeon may either pull shaft 30 relative to a stationary actuator 70, or the surgeon may press actuator 70 over shaft 30. The components may be moved by hand or with a tool, such as a hand-held gun device (similar to a caulk gun), a mechanical lever, a push handle, or a torque wrench device. The actuating tool may be coupled to coupling feature 44 of shaft 30 (FIG. 3).

Moving either shaft 30 or actuator 70 forces second end 54 of expansion sleeve 50 toward first end 52 of expansion sleeve 50 and causes braid 64 of expansion sleeve 50 to expand radially outwardly from shaft 30, as shown in FIG. 2B. Eventually, braid 64 expands and frictionally contacts the inner wall of femur 10 that surrounds the prepared intramedullary canal 13. Therefore, braid 64 should be configured to expand to at least the diameter of the drilled hole in femur 10 to contact the inner wall of femur 10 that surrounds the prepared intramedullary canal 13. Also, braid 64 may be configured to expand beyond the diameter of the drilled hole in femur 10, such as to a diameter of approximately 0.5", 0.6", 0.7", 0.8", 0.9", 1.0", or more. If braid 64 includes strands 65 that are arranged axially, those strands 65 may project outwardly like fins to engage the bone of femur 10. Because shaft 30 is rotatably and axially locked to expansion sleeve 50, shaft 30 becomes frictionally locked within the prepared intramedullary canal 13 of femur 10.

It is within the scope of the present invention that expansion sleeve 50 may be provided with an outer sleeve (not shown) that surrounds expansion sleeve 50 to contact the bone of femur 10. In this embodiment, the outer sleeve and not expansion sleeve 50 would contact the bone of femur 10. The outer sleeve 50 may be a disposable component that prevents bone fragments and debris from entering between strands 65 of expansion sleeve 50.

While expanding expansion sleeve 50, fins 63 of sliding washer 62 may be pressed against exterior surface 11 of the distal portion of femur 10, as shown in FIG. 8. Fins 63 may cut into exterior surface 11 of femur 10 along the opening of the prepared intramedullary canal 13, acting as cleats that prevent rotation of orthopedic guide assembly 20 within the prepared intramedullary canal 13. If additional support is needed to prevent rotation of orthopedic guide assembly 20 within the prepared intramedullary canal 13, it is within the scope of the present invention that actuator 70 may include a pilot hole so that femur 10 may temporarily receive a screw or pin.

According to an exemplary embodiment of the present invention, braid 64 of expansion sleeve 50 is configured to contact the bone of femur 10 while minimizing cutting into the bone, which could make retraction difficult, invasive, and traumatizing. For example, strands 65 of braid 64 may include flat wires that maintain adequate surface contact and friction with the bone of femur 10 with minimum cutting into the bone of femur 10.

Also, as braid 64 expands outwardly and contacts femur 10, braid 64 exerts a radial force against the inner wall of femur 10 that surrounds the prepared intramedullary canal 13. Advantageously, the radial force from braid 64 promotes even contact between expansion sleeve 50 and the bone of femur 10 which centers shaft 30 of orthopedic guide assembly 20 within femur 10. For example, in an exemplary embodiment, the radial force from braid 64 centers and aligns shaft 30 of orthopedic guide assembly 20 with anatomic axis 12 of femur 10.

According to an exemplary embodiment of the present invention, the surgeon is able to customize the expansion of expansion sleeve 50 to accommodate a patient's particular needs. As shown in FIGS. 2A and 2B, the radial distance that expansion sleeve 50 expands from shaft 30 depends on the axial distance that the surgeon translates shaft 30 or actuator 70 relative to the other component. For example, each time the surgeon moves locking assembly 75 of actuator 70 over a tooth 42 of shaft 30, expansion sleeve 50 increases in diameter. Therefore, if the patient has poor bone quality, for example, expansion sleeve 50 may be expanded to a first diameter to compress the patient's bone and then to a second diameter to adequately frictionally contact the compressed bone. As mentioned above, second end 34 of shaft 30 may include a linear reference scale (not shown) so that the surgeon is able to determine the radial expansion of expansion sleeve 50 based on the axial position of actuator 70 relative to shaft 30. From this reading, the surgeon may also be able to evaluate the patient's bone quality. For example, the surgeon may diagnose poor bone quality if significant radial expansion of expansion sleeve 50 is required to adequately engage the bone of femur 10. The surgeon may also visually evaluate the size and condition of intramedullary canal 13 by viewing the expanded expansion sleeve 50 using an X-ray, for example.

According to another exemplary embodiment of the present invention, bands 66 and discrete braid segments 64a-f allow the surgeon to customize the expansion of expansion sleeve 50 to accommodate a patient's particular needs. These discrete braid segments 64a-f may be arranged to accommodate the local bone quality and geometry of femur 10, while still being actuated by movement of a single actuator 70. For example, as discussed above with respect to FIG. 2B, longer braid segments 64a-c may be located in wide portions of the prepared intramedullary canal 13 to achieve more radial expansion than shorter braid segments 64d-f, which may be located in narrow portions of the prepared intramedullary canal 13.

According to yet another exemplary embodiment of the present invention, radial expansion of discrete braid segments 64a-f may provide a tighter fit between orthopedic guide assembly 20 and femur 10 by pulling orthopedic guide assembly 20 axially into the prepared intramedullary canal 13 of femur 10 during expansion. For example, if braid segments 64a-f are sequenced by length, getting progressively shorter from first end 52 to second end 54 of expansion sleeve 50, radial expansion of braid segments 64a-f will occur sequentially. A segment of braid 64 having a high slenderness ratio will buckle and expand before a segment having a low slenderness ratio. The slenderness ratio of each segment is a function of the length of the segment divided by the radius of the segment. The longest braid segment 64a located near first end 52 of expansion sleeve 50 has the highest slenderness ratio and will expand first. After the first braid segment 64a expands, the second braid segment 64b will expand, and so on, thereby pulling orthopedic guide assembly 20 axially into the prepared intramedullary canal 13 of femur 10. The shortest braid segment 64f located near second end 54 of expansion sleeve 50 has the lowest slenderness ratio and will expand last.

According to yet another exemplary embodiment of the present invention, orthopedic guide assembly 20 may be able to bend or flex within a bent intramedullary canal 13 of femur 10. More particularly, the flexible outer perimeter of orthopedic guide assembly 20 defined by expansion sleeve 50 may be able to bend or flex within a bent intramedullary canal 13 of femur 10. In this embodiment, shaft 30 and expansion sleeve 50 may avoid applying focused forces to femur 10 along the bend and may avoid becoming lodged along the bend.

After expansion sleeve 50 is fully expanded into contact with femur 10, any tools used to move actuator 70 may be removed from orthopedic guide assembly 20. Then, the surgeon couples guide component 90 to shaft 30, as shown in FIG. 9. According to an exemplary embodiment of the present invention, guide component 90 includes a sleeve sized to fit over shaft 30, a detent mechanism, or another suitable fastening mechanism for removably coupling guide component 90 to shaft 30. For example, like actuator 70, guide component 90 may be configured to engage teeth 42 of shaft 30. Optionally, guide component 90 may include post 92. In this embodiment, guide component 90 may be impacted to fully seat post 92 in femur 10. However, with shaft 30 anchored securely within the prepared intramedullary canal 13 of femur 10, impaction may be avoided, thereby reducing trauma to the distal portion of femur 10.

Referring to FIGS. 9 and 10, with expansion sleeve 50 and shaft 30 positioned within the prepared intramedullary canal 13 of femur 10, guide component 90 rests against the distal exterior surface 11 of femur 10. According to an exemplary embodiment of the present invention, shaft 30 properly orients guide component 90 with respect to the distal portion of femur 10. More particularly, shaft 30 extends along anatomic axis 12 of femur 10 to properly orient guide component 90 with respect to mechanical axis 14 of femur 10 (FIG. 1).

Then, the surgeon uses guide component 90 to prepare the distal portion of femur 10 for receiving a femoral implant (not shown). As shown in FIG. 10, guide component 90 includes anterior guide slot 94 that is sized to receive oscillating saw 102 or another suitable cutting tool for resecting an anterior surface of femur 10. Guide component 90 may include other guide slots to resect distal and posterior surfaces of femur 10, or guide component 90 may be removed and replaced with other guide components having such features. Guide component 90 may also include guide holes (not shown) for drilling anchor holes into the distal portion of femur 10. Upon implantation of the femoral implant (not shown), these anchor holes in the distal portion of femur 10 will receive stems or posts from the femoral implant to stabilize the femoral implant.

Finally, the surgeon may remove orthopedic guide assembly 20 from femur 10. To remove shaft 30 and expansion sleeve 50 of orthopedic guide assembly 20, the surgeon presses release button 78, allowing expansion sleeve 50 to return freely to its natural, contracted state. If necessary, the surgeon may also pull actuator 70 away from femur 10. If expansion sleeve 50 does not contract freely or by pulling actuator 70, the surgeon may unscrew shaft 30 from expansion sleeve 50 to aid in the removal of expansion sleeve 50. It is within the scope of the present invention that some or all components of orthopedic guide assembly 20 may be disposable to ensure quality and sterility.

Figure 15:
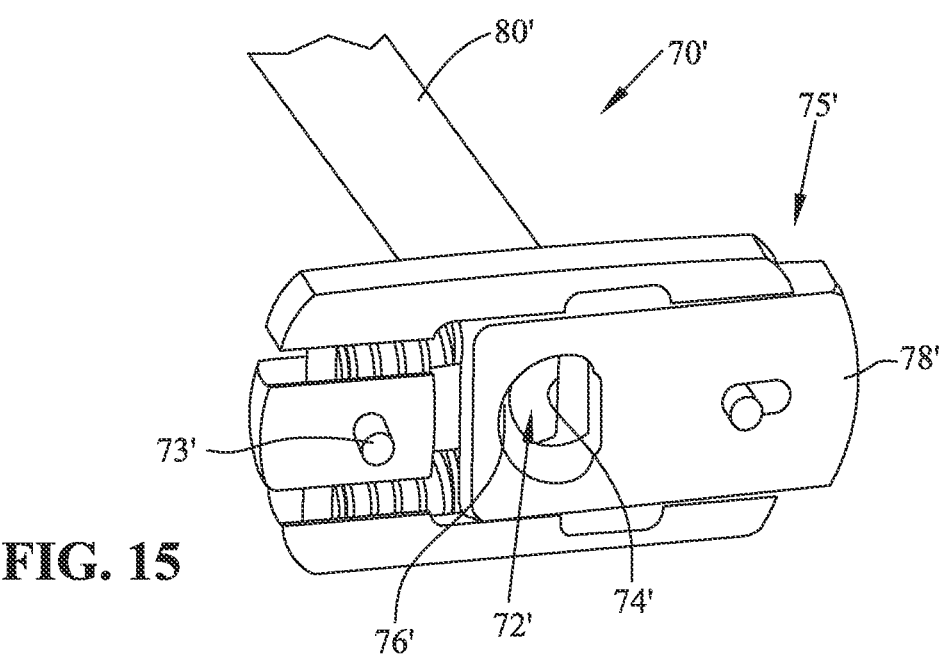
FIG. 15 is a perspective view of the actuator of FIG. 11A.

Another exemplary orthopedic guide assembly 20' is illustrated in FIGS. 11A-15. Orthopedic guide assembly 20' is substantially similar to orthopedic guide assembly 20 of FIGS. 2A-6, with like reference numerals indicating like elements, except as described below. Orthopedic guide assembly 20' includes shaft 30' (FIG. 12), expansion sleeve 50' (FIGS. 13 and 14), and actuator 70' (FIG. 15).

Expansion sleeve 50' of orthopedic guide assembly 20' is biased naturally in a partially radially expanded state, as shown in FIG. 13. Expansion sleeve 50 of orthopedic guide assembly 20, on the other hand, is biased naturally in a contracted state, as shown in FIG. 4. As shown in FIG. 13, expansion sleeve 50' includes two annular bands 66' that divide braid 64' into three braid segments 64*a-c*', although the number of bands 66' may vary. Each band 66' of FIG. 13 is constructed of wire that is wrapped around braid 64'.

In operation, orthopedic guide assembly 20' may be adjusted from a first, insertion or contracted position, as shown in FIG. 11A, to a second, expanded position, as shown in FIG. 11B. In the insertion position of FIG. 11A, the surgeon pulls actuator 70' toward second end 34' of shaft 30' to axially extend expansion sleeve 50', forcing expansion sleeve 50' radially inwardly toward shaft 30'. In the expanded position of FIG. 11B, the surgeon may release actuator 70', allowing expansion sleeve 50' to return to its naturally expanded state. It is also within the scope of the present invention that the surgeon may push actuator 70' toward first end 32' of shaft 30' to axially compress expansion sleeve 50', forcing expansion sleeve 50' to expand further radially outwardly from shaft 30'.

Unlike actuator 70 of FIG. 6, actuator 70' of FIG. 15 includes an elongate sleeve 80' that surrounds shaft 30'. After expansion sleeve 50' is fully expanded into contact with femur 10, the surgeon may couple guide component 90 (FIG. 9) onto sleeve 80' rather than coupling guide component 90 directly onto shaft 30'. Sleeve 80' may accommodate guide components 90 of various sizes.

While this invention has been described as having preferred designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An expandable rod sized for insertion into a patient's bone, the expandable rod comprising:
    a shaft having a first end and a second end, wherein a portion of the shaft comprises a flat surface and a plurality of teeth comprising blocking faces oriented towards the first end of the shaft;
    an expansion member coupled to and adjustable along the shaft between a first, contracted state and a second, expanded state, the expansion member configured to expand radially outwardly from the contracted state to the expanded state, the expansion member including a first expansion segment and a second expansion segment, the first expansion segment having a higher slenderness ratio than the second expansion segment; and
    an actuator coupled to one end of the expansion member, wherein the actuator comprises:
        a central channel that receives the shaft such that the actuator is moveable along the shaft to adjust the expansion member between the contracted state and the expanded state;
        a cam biased toward the shaft and configured to slide over the plurality of teeth as the actuator moves along the shaft toward the first end and to catch on the blocking faces to prevent the actuator from moving toward the second end of the shaft;
        a release button configured to, when pressed, cause the cam to disengage from one of the blocking faces of the plurality of teeth to allow the actuator to move toward the second end of the shaft; and
        first and second circular surfaces connected by a cylindrical surface,
        wherein the central channel is aligned with and passes through a center of the first circular surface and a center of the second circular surface, wherein the release button is arranged in a slot in and protrudes radially outward from the cylindrical surface, and wherein the central channel comprises a flat wall that cooperates with the flat surface of the shaft to prevent the actuator and the shaft from rotating relative to one another.

2. The expandable rod of claim 1, wherein the first expansion segment expands from the contracted state to the expanded state before the second expansion segment expands from the contracted state to the expanded state.

3. The expandable rod of claim 1, wherein the expansion member is a braided construct.

4. The expandable rod of claim 1, wherein a first length of the first expansion segment is greater than a second length of the second expansion segment.

5. The expandable rod of claim 1, wherein, when the expansion member is in the expanded state, the first expansion segment has a larger diameter than the second expansion segment.

6. The expandable rod of claim 1, wherein the expansion member further comprises at least a third expansion segment having a lower slenderness ratio than the second expansion segment, the first, second, and third expansion segments configured to expand sequentially from the contracted state to the expanded state.

7. The expandable rod of claim 1, wherein the first expansion segment is nearer to the first end of the shaft than the second expansion segment.

8. The expandable rod of claim 1, further comprising a non-expandable, intermediate segment located axially between the first and second expansion segments.

9. The expandable rod of claim 8, wherein the intermediate segment comprises an annular band that surrounds the expansion member to restrict expansion of the expansion member between the first and second expansion segments.

10. The expandable rod of claim 9, wherein the annular band is moveable axially along the expansion member to adjust a length of at least one of the first and second expansion segments.

11. An expandable rod sized for insertion into a patient's bone, the expandable rod comprising:
a shaft having a first end and a second end, wherein a portion of the shaft comprises a flat surface and a plurality of teeth comprising blocking faces oriented towards the first end of the shaft;
an expansion member coupled to and adjustable along the shaft between a first, contracted state and a second, expanded state, the expansion member configured to expand radially outwardly from the contracted state to the expanded state, the expansion member including a first expansion segment and a second expansion segment, the first expansion segment having a higher slenderness ratio than the second expansion segment; and
an actuator coupled to one end of the expansion member, wherein the actuator comprises:
a central channel that receives the shaft such that the actuator is moveable along the shaft to adjust the expansion member between the contracted state and the expanded state, wherein the central channel comprises a flat wall that cooperates with the flat surface of the shaft to prevent the actuator and the shaft from rotating relative to one another; and
a cam biased toward the shaft and configured to slide over the plurality of teeth as the actuator moves along the shaft toward the first end and to catch on the blocking faces to prevent the actuator from moving toward the second end of the shaft; and
a guide component coupled to the expandable rod, the guide component configured to reference an exterior surface of the patient's bone when the expandable rod is positioned within an intramedullary canal of the patient's bone.

12. An expandable rod sized for insertion into a patient's bone, the expandable rod comprising:
an expansion member having a first end and a second end;
a shaft coupled to the expansion member, wherein a portion of the shaft comprises a flat surface and a plurality of teeth comprising blocking faces oriented towards the first end of the expansion member; and
an actuator moveably coupled to the shaft and to the second end of the expansion member, the actuator configured to move the second end of the expansion member axially toward the first end of the expansion along the shaft member to compress the expansion member axially and to expand the expansion member radially outwardly, the first end of the expansion member configured to expand before the second end of the expansion member expands, wherein the actuator comprises:
a central channel that receives the shaft; and
a cam biased toward the shaft and configured to slide over the plurality of teeth as the actuator moves along the shaft toward the first end of the expansion member and to catch on the blocking faces to prevent the actuator from moving toward the second end of the expansion member;
a release button configured to, when pressed, cause the cam to disengage from one of the blocking faces of the plurality of teeth to allow the actuator to move toward the second end of the shaft; and
first and second circular surfaces connected by a cylindrical surface,
wherein the central channel is aligned with and passes through a center of the first circular surface and a center of the second circular surface,
wherein the release button is arranged in a slot in and protrudes radially outward from the cylindrical surface, and
wherein the central channel comprises a flat wall that cooperates with the flat surface of the shaft to prevent the actuator and the shaft from rotating relative to one another.

13. The expandable rod of claim 12, wherein the expansion member defines a bore and the shaft extends through the bore of the expansion member.

14. The expandable rod of claim 12, wherein the first end of the expansion member is axially fixedly coupled to the shaft and the second end of the expansion member is axially movably coupled to the shaft.

15. The expandable rod of claim 12, wherein the first end of the expansion member includes a first expansion segment and the second end of the expansion member includes a second expansion segment, the expansion member further including an non-expandable, intermediate segment located axially between the first and second expansion segments.

16. The expandable rod of claim 12, wherein the first end of the expansion member expands radially outwardly a greater distance than the second end of the expansion member.

17. An expandable rod sized for insertion into a patient's bone, the expandable rod comprising:
a shaft having a first end and a second end, wherein a portion of the shaft comprises a flat surface and a plurality of teeth comprising blocking faces oriented towards the first end of the shaft;

a braided construct expansion member coupled to the shaft and adjustable between a first, contracted state and a second, expanded state, the expansion member configured to expand radially outwardly from the contracted state to the expanded state, the expansion member including a first expansion segment and a second expansion segment, the first expansion segment having a higher slenderness ratio than the second expansion segment;

an intermediate segment located axially between the first and second expansion segments configured to restrict expansion of the expansion member between the first and second expansion segments; and an actuator coupled to one end of the expansion member, wherein the actuator comprises:
- a central channel that receives the shaft such that the actuator is moveable along the shaft to move the actuator from the second end toward the first end to compress the expansion member axially toward the first end of the shaft to adjust the expansion member between the contracted state and the expanded state, the first expansion segment configured to expand before the second expansion segment expands;
- a cam biased toward the shaft and configured to slide over the plurality of teeth as the actuator moves along the shaft toward the first end and to catch on the blocking faces to prevent the actuator from moving toward the second end of the shaft;
- a release button configured to, when pressed, cause the cam to disengage from one of the blocking faces of the plurality of teeth to allow the actuator to move toward the second end of the shaft; and
- first and second circular surfaces connected by a cylindrical surface,
- wherein the central channel is aligned with and passes through a center of the first circular surface and a center of the second circular surface,
- wherein the release button is arranged in a slot in and protrudes radially outward from the cylindrical surface, and
- wherein the central channel comprises a flat wall that cooperates with the flat surface of the shaft to prevent the actuator and the shaft from rotating relative to one another.

18. The expandable rod of claim 17, further comprising a linear reference scale corresponding with the plurality of teeth of the shaft.

19. The expandable rod of claim 17, further comprising an internally threaded plug on the braided construct expansion member configured to engage an external thread of the first end of the shaft.

* * * * *